(12) United States Patent
Barenholz et al.

(10) Patent No.: US 6,924,130 B1
(45) Date of Patent: Aug. 2, 2005

(54) ENZYMATIC TRANSESTERIFICATION OR HYDROLYSIS OF PHOSPHOLIPIDS IN AQUEOUS MEDIA

(75) Inventors: Yechezkel Barenholz, Jerusalem (IL); Shimon Amselem, Rehovot (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 25 days.

(21) Appl. No.: 10/009,771

(22) PCT Filed: Jun. 15, 2000

(86) PCT No.: PCT/IL00/00350

§ 371 (c)(1),
(2), (4) Date: Dec. 13, 2002

(87) PCT Pub. No.: WO00/77183

PCT Pub. Date: Dec. 21, 2000

Related U.S. Application Data
(60) Provisional application No. 60/139,316, filed on Jun. 15, 1999.

(51) Int. Cl.$^7$ ............................. C12N 11/14; C12P 7/64
(52) U.S. Cl. ........................................ 435/134; 435/176
(58) Field of Search ................................ 435/134, 176, 435/458, 68.1

(56) References Cited

U.S. PATENT DOCUMENTS

| | | | | |
|---|---|---|---|---|
| 4,472,503 A | * | 9/1984 | Matsuo et al. | ............... 435/176 |
| 5,418,147 A | * | 5/1995 | Huang et al. | ............... 435/69.1 |
| 5,763,172 A | * | 6/1998 | Magda et al. | ................... 435/6 |

OTHER PUBLICATIONS

Sagatova et al., "Enzymatic Conversion of Phosphatidylcholine to Phosphatidylglycerol", *Applied Bochemistry and Microbiology*, vol. 32, No. 5, pp. 452–456 (1996).

Anthonsen et al., "Phospholipids Hydrolysis in Organic Solvents Catalysed By Immobilised Phospholipase C", *Journal of Molecular Catalysis B: Enzymatic*, vol. 6, No. 1–2, pp. 125–132 (1999).

Rakhimov et al., "Properties of Phospholipase D From *Raphanus–Sativus*", *Biochemistry*, (English translation of Biokhimiya) vol. 46, No. 2 Part 1, pp. 197–204 (1981).

XP 002151651: Abstract for JP 63 036791: "Production of Phospholipids Whose Base . . . ", Nippon Oils & Fats Co Ltd, (1988), Database WPI, week 8813, Derwent Publications Ltd., London.

Allgyer et al., "Phospholipase D from Savoy Cabbage: Purification and Preliminary Kinetic Characterization", *Biochemistry*, vol. 18, No. 2, pp. 5348–5353 (1979).

Bartlett, "Phosphorus Assay in Column Chromatography", *J. Biol. Chem.*, vol. 234, No. 3, pp. 466–471 (1959).

Bligh et al., "A Rapid Method of Total Lipid Extraction and Purification", *Canadian Journal of Biochemistry and Physiology*, vol. 37, No. 8, pp. 911–917 (1959).

Servi, "Phospholipases as Synthetic Catalysts", *Topics in Current Chemistry*, vol. 200, pp. 127–158 (1999).

Amselem et al., "In Vitro Tests to Predict In Vivo Performance of Liposomal Dosage Forms", *Chemistry and Physics of Lipids*, vol. 64, pp. 219–237 (1993).

Barenholz et al., "Chapter 29: Quality Control Assays in the Development and Clinical Use of Liposome–Based Formulations", pp. 527–616 from *Liposome Technology, 2$^{nd}$ Edition Volume I: Liposoms preparation and Related Techniques*, edited by Gregoriadis, London: CRC Press (1993).

Yang, "Phospholipase D From Savoy Cabbage", *Methods in Enzymol*, vol. 14, pp. 208–211 (1969).

* cited by examiner

*Primary Examiner*—David M. Naff
*Assistant Examiner*—Deborah K. Ware
(74) *Attorney, Agent, or Firm*—Browdy and Neimark, P.L.L.C.

(57) ABSTRACT

Methods of conducting phospholipase-catalyzed transesterification or hydrolysis of phospholipids present in aqueous liposomal suspensions, in the absence of detergents and organic solvents, are described. The method, which employs a water/solid particle interface, gives high conversions, particularly when the solid particle is silica gel having a small particle size and is present at a level at least four times the weight of the reacting lipid. The reaction is useful for the preparation of a variety of differently substituted phospholipids, as well as diacyl glycerols and ceramides.

16 Claims, No Drawings

ENZYMATIC TRANSESTERIFICATION OR HYDROLYSIS OF PHOSPHOLIPIDS IN AQUEOUS MEDIA

REFERENCE TO RELATED APPLICATIONS

The present application is the national stage under 35 U.S.C. 371 of international application PCT/IL00/00350, filed Jun. 15, 2000 which designated the United States, and which international application was published under PCT Article 21 (2) in the English language.

FIELD OF THE INVENTION

The present invention relates to method of conducting a phospholipase-catalyzed transesterification or hydrolysis of a phospholipid. The reaction is useful for the preparation of a variety of differently substituted phospholipids, as well as diacyl glycerols and ceramides. The method employs a water/solid particle interface, gives high conversions, and does not require the use of organic solvents, detergents or surfactants.

REFERENCES

Allgyer, T. T. and Wells, M. A., *Biochemistry* 18:5348 (1979).
Amselem, S. et al., *Chem. Phys. Lipids* 64, 219–237 (1993).
Barenholz, Y. and Amselem, S., "Liposome Preparation and Related Techniques", pp. 527–616, in *Liposome Technology*, $2^{nd}$ ed., Vol. 1, G. Gregoriadis, ed., CRC Press, Boca Raton, Fla., 1993.
Bartlett, G. R., *J. Biol. Chem.* 234:466–71 (1959).
Bligh, E. G. and Dyer, W. J., *Can. J. Biochem.* 31:911 (1959).
Servi, S., *Topics in Current Cherntry* 200:127–158 (1999).
Yang, S. F., *Methods in Enzymol.* 14:208–211 (1969).

BACKGROUND OF THE INVENTION

Phospholipases A1, A2, C, and D enzymatically cleave the bonds in a diacyl phospholipid as illustrated below:

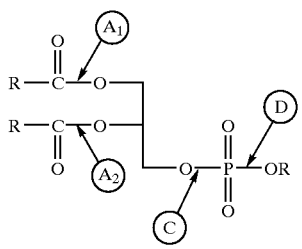

These enzymes have proven useful in the synthetic preparation of a wide variety of phospholipids, sphingolipids, and neutral lipids, and in particular the preparation of new, non-naturally occurring, or non-abundant lipids from more abundant source materials. Similarly, C- and D-type phospholipases which use sphingomyelin as a substrate (sphingomyelin phosphodiesterases), and various glycosidases which use glycolipids as substrates, can be utilized to prepare ceramides and other lipids.

In particular, phospholipase D has been used to convert phosphatidyl cholines (PC) to less common lipids such as phosphatidyl serines (PS) and phosphatidyl glycerols (PG). The reaction is a transesterification (also referred to as transphosphatidylation) between the starting material, PC, and a hydroxyl containing reagent such as glycerol or serine. The enzyme is especially useful in this respect in that it is able to produce the transesterified product in the presence of more than a stoichiometric amount of water (Servi). An organic solvent or detergent is typically required, as the lipid substrate is not water-soluble, and when lipid is presented to the enzyme in the form of an aqueous liposomal dispersion, the enzymatic activity is usually poor. Conventional methods for this reaction have generally employed a two-phase system containing water, in which the enzyme is soluble, and an organic solvent, in which the lipid is soluble, with the enzymatic reaction occurring at the interface between the water and the organic solvent.

The use of detergents or organic solvents is problematic in large scale reactions, and may be prohibited in the production of many pharmaceutical and food products. In addition, some amount of the hydrolysis product, phosphatidic acid (PA), is typically formed in such reactions, and methods are sought for increasing conversion to the transesterification product.

SUMMARY OF THE INVENTION

The present invention includes, in one aspect, a method of conducting an enzyme-catalyzed transesterification or hydrolysis of a phospholipid or glycolipid. The method comprises dissolving the enzyme in an aqueous medium containing a liposomal suspension of the lipid and a hydroxyl-containing reagent, adding silica gel to the medium, and agitating the resulting mixture. For some enzymes, a divalent metal cation, such as $Ca^{+2}$, $Zn^{+2}$, or $Mg^{+2}$, is required for reaction. The enzyme is preferably a phospholipase, such as phospholipase A1, A2, C, or D, or a sphingomyelin phosphodiesterase. In a preferred embodiment, the phospholipase is phospholipase D.

The method is particularly useful for reactions of phospholipids which make up naturally occurring phospholipid mixtures, such as phosphatidyl cholines, or for phospholipids isolated from tissue, e.g. a brain phospholipid extract. The hydroxyl-containing reagent can be water, in the case of a hydrolysis reaction; in preferred embodiments, the reagent is an alcohol or alcohol derivative, such as glycerol, serine, inositol, or hydroxy-terminated PEG (polyethylene glycol). Synthetic phospholipids of various stereochemistries can be prepared by varying the stereochemistry of the hydroxyl-containing reagent, e.g. in the case of serine.

In the reaction, the silica gel is preferably added in an amount which is at least four times the amount of the lipid by weight, giving a silica gel/lipid ratio of at least 4:1, and more preferably an amount which is at least ten times the amount of the lipid by weight, giving a silica gel/lipid ratio of at least 10:1. The silica gel preferably has a mean particle size no greater than 25 $\mu$m, and more preferably no greater than 15 $\mu$m.

In further preferred embodiments, the concentration of phospholipase in the medium is at least 3mg/ml, and more preferably at least 7 mg/mm. When the enzyme is phospholipase D, the concentration of calcium ion in the medium is preferably in the range of 5–100 mM.

These and other objects and features of the invention will be made more fully apparent in the following detailed description of the invention.

DETAILED DESCRIPTION OF THE INVENTION

1. Definitions

The terms below have the following meanings unless indicated otherwise.

A "phospholipid" refers to an amphipathic lipid having one or two hydrophobic acyl chains and a phosphate-containing polar head group. The lipid may contain a chemically reactive group, such as an amine, acid, ester, aldehyde or alcohol, at the polar head group. Synthetic phospholipids may also have a chromophore or a fluorophore attached at various parts of the molecule.

The hydrocarbon chains are typically between about 2–26, and preferably about 14–22, carbon atoms in length, and commonly have varying degrees of unsaturation. The hydrocarbon chains may include branching or other modifications, e.g. cyclopropyl or cyclohexyl groups.

Representative examples of phospholipids are phosphatidyl choline (PC), phosphatidyl ethanolamine (PE), phosphatidic acid (PA), phosphatidyl inositol (PI), phosphatidyl glycerol (PG), and sphingomyelin (N-acyl sphingosylphosphocholine, a sphingolipid). The backbone in sphingolipids is derived from sphingosine, rather than from glycerol. In sphingomyelin, the amino group of sphingosine is linked to a fatty acid chain via an amide bond, and the primary hydroxyl group is esterified to phosphoryl choline.

An unusual type of phospholipid is found in the membranes of archaea, a type of bacteria. The cell membranes of these organisms are composed of phytanyl lipids, rather than fatty acids. The phytanyl (3,7,11,15-tetramethylhexadecyl) lipids are joined to glycerol to form lipids by an ether rather than an ester bond.

The name of a particular lipid includes the specific acyl groups, e.g. dimyristoyl phosphatidyl choline (DMPC) or N-palmitoyl sphingomyelin. Naturally occurring lipid mixtures are common, and these include the lecithins, such as soy lecithin or egg lecithin, which are mixtures of phosphatidyl cholines having various acyl chains. Such mixtures may be used in the present reaction, as well as partially purified tissue extracts.

A "phospholipase" is an enzyme that cleaves (by hydrolysis or tranesterification) ester bonds in phospholipids. The two general types are aliphatic esterases (types A1, A2 and B), which release fatty acids from glycerol-based phospholipids, and phosphodiesterases (types C and D), which cleave phosphate ester bonds. Spingomyelinases (sphingomyelin phosphodiesterases) may be similar or identical to phospholipases which act on glycerophospholipids, as in many bacterial enzymes, or they may be specific for sphingolipids, as in eukaryotic enzymes. As used herein, the category of C- and D-type phospholipases includes sphingomyelin phosphodiesterases.

"Silica gel" refers to a colloidal, highly adsorbent form of silicon dioxide or a salt (silicate) thereof. The term as used herein covers commercial silica gels used for chromatography, preferably TLC grade, which may comprises silicic acid ($SiO_2 \cdot nH_2O$) or a salt such as magnesium silicate (e.g. Florisil™).

An "alcohol derivative" is an organic alcohol (ROH, where R is aryl, alkyl or cycloalkyl, and preferably alkyl or cycloalkyl) where the group R may be further substituted with a group selected from, e.g., hydroxy, alkoxy, amino, alkylamino, carboxylic acid, carboxylic ester, keto, aldehyde, nitro, cyano, imino, thio, alkylthio, sulfonic acid or ester, or phosphonic acid or ester. Preferred alcohol derivatives include alcohol-substituted amino acids, glycols, and sugars. Also preferred are hydroxy-terminated polyalkylene oxides, such as polyethylene oxide, having molecular weights in the range of about 300 to 40,000. In general, preferred compounds have at least 5% (w:w) aqueous solubility; however, less soluble alcohols or alcohol derivatives may also be used.

II. Phospholipase-Catalyzed Reactions Employing a Solid Particle Interface

Certain types of solid particles can promote reaction of phospholipids with phospholipases by providing an interface between the lipids, which adsorb to the particles, and the enzyme, which remains predominantly in the aqueous phase. The solid interface may also serve to activate the enzyme. It is possible that immobilization of the enzyme and binding of substrate together on the particle surface results in a change in the conformation of the phospholipase and its conversion to an activated state.

As an example of this method, phospholipase D-catalyzed conversion of egg phosphatidyl choline (PC) to the corresponding phosphatidyl glycerol (PG) was carried out in an aqueous medium using various solid adsorbents in place of the organic solvents (such as diethyl ether) used conventionally. General procedures for small scale reactions are as follows.

Reagents include acetate buffer (pH 5.6) containing 50–200 mM $CaCl_2$, glycerol at a concentration of about 25–75% by volume, egg phosphatidylcholine (PC), and phospholipase D. The enzyme may be obtained commercially or prepared as described in Example 1. The substrate (PC) is dispersed in glycerol-acetate buffer, preferably as multilamellar vesicles (MLV), at a concentration of about 5 mg/ml. The MLV may be prepared by hydration of a dry lipid film, the more conventional method, or by reverse evaporation (REV) using a high lipid concentration in a solvent such as ether or a Freon®. In this technique, a nonaqueous solution of vesicle-forming lipids is dispersed with a smaller volume of an aqueous medium to form a water-in-oil emulsion. After removal of the lipid solvent, the resulting gel is converted to liposomes.

Phospholipase D is added to the liposomal dispersion, and the mixture is vortexed until all the enzyme is in solution. The reaction is initiated by adding the solid adsorbent at room temperature, and shaking is commenced immediately.

In one procedure, the reaction is terminated by adding chloroform and methanol to give a final solvent ratio of about 1:1:1 (chloroform:methanol:water). The phases are separated, e.g. by centrifugation, and the phospholipids are isolated from the lower chloroform phase. The products may be separated by preparative TLC chromatography on Unlatch silicic acid glass plates, using a solvent system of chloroform:acetone:methanol:acetic acid:water (6:8:2:2:1).

Alternatively, for preparation of products to be used in food or drugs, where the use of solvents such as chloroform is to be avoided, the lipids may be extracted from the reaction mixture using hexane, heptane, ethanol/hexane or ethanol/heptane mixtures, under either acidic or neutral conditions. If desired, $Ca^{+2}$ ions can be removed from the product lipids by a chelating agent such as EDTA, which will partition into the aqueous phase.

The level of conversion to phosphatidyl glycerol (PG) is determined by TLC followed by phosphorus content analysis, by using a refractive index or light scattering detector, or by the use of radioactively labeled glycerol, as described in Example 2. Amine lipid products may also be assayed colorimetrically by reaction with picryl sulfonate (TNBS).

Results of the reaction using various solid adsorbents, at a ratio of about 70 mg adsorbent per mg lipid, are given in Table 1. The Table shows conversions to PG and to PS in reactions of PC with glycerol and serine, respectively. It is clear that, among the adsorbents tested, silica gel was the most effective.

TABLE 1

Activation of Phospholipase D by Solid Adsorbents

| Adsorbent | % Conversion (±5) | |
|---|---|---|
| | PG | PS |
| Silica gel (Kieselgel® 60 Merck) | 90 | 65 |
| Kieselguhr® (BDH) | 70 | 50 |
| Celite® (Koch-light) | 40 | — |
| Super-cel® (Amend) | 20 | — |
| None | 0 | 0 |

In further experiments, various types and particle sizes of silica gel and other adsorbents were tested for their activity in the enzymatic conversion of PC to PG. Each reaction system contained 10 mg PC dispersed in 0.5 ml acetate buffer (pH 5.60) containing 25% (vol) glycerol and 50 mM $CaCl_2$. Cabbage phospholipase D (0.5 mg, Boehringer) was added, and the reaction was initiated by adding 0.2 grams adsorbent. The mixtures were shaken for 30 minutes at room temperature.

The results are shown in Table 2. As can be seen from this Table, the best conversions were obtained with TLC grade silicic acid (from Merck, Philadelphia, Pa., and Camag, Muttenz, Switzerland) (50–60% conversion to PG) and with TLC magnesium silicate from Bio-Rad (Richmond, Calif.) (50% conversion).

A correlation between the particle size of the silicic acid and conversion was found, with smaller particle sizes giving higher yields. The best results in this series were obtained with silica gel 60H and HR, TLC Grade (Merck), which have the finest particles (particle size distribution 5–20 μm, mean particle size 10–12 μm). TLC grade magnesium silicate from Bio-Rad (Richmond, Calif.) also gave good conversion (particle size distribution 2–44 μm). A much larger particle size magnesium silicate, used in column chromatography, gave only 20% conversion (Florisil® entry in Table 2). Accordingly, preferred mean particle sizes of silica gel (silicic acid or magnesium silicate) for use in the reactions described herein would be less than 25 μm, and preferably less than 15 μm.

With aluminum oxide adsorbents (neutral, acidic or basic alumina) very low conversions were achieved (5–15% PG). When adsorbent materials such as Bio-Beads® SM-2 from Bio-Rad or Chelex® (chelating resin) from Sigma were used, no conversion was obtained.

TABLE 2

Effect of Different Types and Sizes of Adsorbents on PC → PG Conversion

| | Adsorbent | PG (±10%) |
|---|---|---|
| Silicic Acid | Merck Silica gel H/HR, TLC grade (5–20 μm) | 60 |
| | Merck Silica gel mesh <230 (>60 μm) | 50 |
| | Merck Silica gel mesh 70–230 (60–210 μm) | 40 |
| | Merck Silica gel extra pure mesh 70–230 | 40 |
| | Merck Silica gel mesh 35–70 (210–500 μm) | 30 |
| | Sigma, Silica gel, mesh 325 (ca. 40 μm) | 40 |
| | Sigma, Silica gel, mesh 60–200 (75–250 μm) | 10 |
| | CAMAG, Silica gel for TLC | 50 |
| | Bio-Rad, Bio-Sil® for TLC | 40 |
| | BDH, Silica gel, 6–20 mesh (>840 μm) | 5 |
| | BDH Sand | 10 |
| Mg Silicate | Bio-Rad (2–44 μm) | 50 |
| | Florisil® (column chromatography grade) | 20 |
| Aluminum oxide | Bio-Rad, neutral alumina | 15 |
| | Merck, neutral alumina | 5 |
| | Sigma, acidic alumina | 5 |
| | Basic alumina | 0 |
| Bio-Beads® | SM-2 Bio-Rad | 0 |
| Chelex® | chelating resin (Sigma) | 0 |

It was also found that, for a given amount of enzyme, the percentage of transphosphatidylation increased with the amount of silica gel per milligram phospholipid, as shown in Table 3.

TABLE 3

Effect of Amount of Silica Gel on PC→PG Conversion

| Mg adsorbent/mg phospholipid | % PC to PG Conversion (±10%) |
|---|---|
| 20 | 20 |
| 40 | 60 |
| 60 | 90 |

The effect of varying the amount of silica gel was further investigated in the 500 mg scale reactions described below. Again, conversion increased with an increase in silica gel:lipid ratio. Conversion appeared to level off at a ratio of approximately 10:1 (Table 4); however, the difference between the last two ratios tested (9/1 and 11/1) is not substantial. Reactions were also performed on a 20 g scale at silica/PC ratios of 5 and 25; conversions obtained were 40% and 60%, respectively.

Based on these results, it appears that yields generally increase with silica gel/lipid ratio. Accordingly, ratios of at least 4/1, and more preferably at least 10/1, are preferred. In some cases, such as shown in Table 4, conversion appeared to level off, but no adverse effects of increasing the silica gel/lipid ratio were observed in any case.

TABLE 4

Effect of Amount of Silica Gel on 500 mg Scale PC→PG Conversion

| Silica Gel/PC Ratio | PG Formulation (% ±10) |
|---|---|
| 3.3 | 24 |
| 6.7 | 28 |
| 9 | 40 |
| 11 | 40 |

Reaction conditions: enzyme concentration = 7.5 mg/ml; buffer = 40 mM acetate, pH 5.6, containing 50% glycerol v/v 100 mM $Ca^{++}$; reaction time = 20 hours, rt.

II. Effect of Other Reaction Variables on Conversion

The effects of other parameters on the representative egg PC→PG reaction were also studied. These variables included enzyme concentration, glycerol concentration, pH, $Ca^{+2}$ concentration, liposome size, order of reagent addition, lipid composition, presence of antioxidants, enzyme source and preparation, and age of enzyme preparation.

Most of the reactions in these studies were carried out on a larger scale, using 500 mg to 5 g of lipid. The following procedure was used for the mid-scale reaction. Egg phosphatidylcholine (500 mg) was dissolved in chloroform, which was then evaporated by a stream of $N_2$. The dried lipid was dispersed in 10 ml acetate buffer (40 mM, pH 5.6) containing 50% glycerol (v/v) and $CaCl_2$ (100 mM). Multilamellar vesicles (MLV) were formed by vigorous shaking of the suspension, using a Lab Line multi wrist shaker (speed setting=7) at room temperature, until all the lipid was incorporated in the liposomal dispersion. Alternatively, MLV can be prepared by reverse evaporation (REV), as described above.

Phospholipase D (lyophilized powder, 50 mg) was added to the liposomal dispersion and the mixture vortexed until all the enzyme was in solution. The reaction was initiated by adding silicic acid (3 grams, Kieselgel® 60 Merck) at room temperature, and shaking was commenced immediately. The reaction was terminated by adding chloroform and methanol to give a final solvent ratio of 1:1:1 chloroform:methanol:water. Two phases formed after vortexing and were separated by centrifugation at 1000 g. The phospholipids were isolated from the lower chloroform phase by preparative TLC chromatography on Analtech silicic acid glass plates, using a solvent system of chiloroform:acetone:methanol:acetic acid:water (6:8:2:2:1).

A. Enzyme Concentration

Table 5 shows the effect of varying enzyme concentration. The optimum concentration under these conditions was about 7 mg/ml. Above this concentration a plateau in the PG formation was obtained.

TABLE 5

Effect of Enzyme Concentration of PG Formation

| Enzyme Concentration (mg/ml) | PG Formation (% ±10) |
|---|---|
| 0.5 | 21 |
| 1 | 31 |
| 3 | 36 |
| 7.5 | 42 |
| 15 | 40 |
| 15 (stepwiseaddition) | 40 |

Reaction conditions: Buffer = 40 mM Acetate, pH 5.6, containing 50% glycerol v/v and 100 mM $Ca^{++}$; lecithin/silica gel ratio = 0.15; reaction time = 20 hours; room temperature; reaction volume = 10 ml.

B. Glycerol Concentration

Effect of glycerol concentration is shown in Table 6. The product, PG, was formed in greater amounts and at a higher rate at lower glycerol concentrations (Table VI). It is possible that high glycerol concentrations increase the viscosity of the incubation medium, thus decreasing the rate of PG formation, or that the glycerol coats the silica gel. However, not unexpectedly, less of the hydrolysis product (PA) was formed at higher glycerol concentrations.

TABLE 6

Effect of Glycerol Concentration on PG Formation

| Glycerol Concentration (% v/v) | PG Formation (% ±10) | PA Formation (% ±3) |
|---|---|---|
| 25 | 70 | 10 |
| 50 | 40 | 7 |
| 75 | 15 | 4 |

Reaction conditions: enzyme concentration = 7.5 mg/ml; buffer = 40 mM acetate pH 5.6 100 mM $Ca^{++}$; lecithin/silica gel ratio = 0.15; reaction time = 20 hours; room temperature C. $Ca^{+2}$ Concentration: pH Based on the data in Table 7, the optimal $Ca^{+2}$ concentration for the phospholipase D-catalyzed transphosphatidylation reaction under these conditions appeared to be about 50–100 mM. However, some preparations worked well at $Ca^{+2}$ concentrations of 5 mM or even lower. Other phospholipases may require different ions, such as $Mg^{+2}$ (for C-type sphingomyelinases) or $Zn^{+2}$, and some have no ion requirement.

TABLE 7

Effect of $Ca^{+2}$ Concentration

| Incubation Buffer, mM $CaCl_2$ | PG Formation (% ±10) | PA Formation (% ±3) |
|---|---|---|
| 50 | 37 | 3 |
| 100 | 40 | 4 |
| 150 | 28 | 3 |
| 200 | 21 | 3 |

Reaction conditions: enzyme concentration = 5 mg/ml lecithin/silica gel ratio = 0.11; buffer = 40 mM Tris pH 8.5; reaction time = 20 hours: room temperature.

Similar PG conversions were obtained using Tris buffer (pH 8.5) and acetate buffer (pH 5.6). However, somewhat less PA was formed at pH 8.5 (Table 8).

TABLE 8

Effect of pH

| Incubation Buffer | PG Formation (% ±10) | PA Formation (% ±3) |
|---|---|---|
| Acetate, pH 5.6 | 59 | 14 |
| Tris, pH 7.5 | 38 | 10 |
| Tris, pH 8.5 | 60 | 10 |

Reaction conditions: enzyme concentration = 7.5 mg/ml, lecithin/silica gel ratio = 0.15; reaction time = 20 hours; room temperature.

D. Source of Enzyme

The enzymatic activities of different batches of phospholipase D, prepared in-house from cabbage as described in Example 1, were compared to the activities of phospholipase D from various commercial sources. Cabbage phospholipase D from Boehringer Co. (Indianapolis, Ind.) showed a markedly superior activity to the in-house preparations and to phospholipase obtained from Sigma Co. (St. Louis, Mo.), giving similar yields of PG from PC with only one-fifth of the amount of enzyme (PC/enzyme=25:1). Phosphatidic acid (PA) was formed with all the enzymes (5–15% relative to total phospholipid).

In view of the superior enzymatic activity of the commercial phospholipase D from the Boehringer Co., additional purification of in-house cabbage phospholipase D preparation was carried out, following the procedure described by Allgyer and Wells. However, no increase in the transphosphatidylation specific activity of the in-house phospholipase was obtained.

E. Age of Enzyme Preparation: Transferase/Hydrolase Activity

It is generally observed that the transferase activity of phospholipase D is less stable than its hydrolase activity. Thus, the ratio of transferase/hydrolase activity of the enzyme tends to diminish with time after its preparation. This variation in transferase/hydrolase activity has been a source of irreproducibility from one preparation of enzyme to another. In reactions conducted by the authors using the biphasic ether/water system, phospholipase D from Savoy cabbage lost its transferase activity by at least 20% per month even upon storage at −20° C., and much more when stored at 4° C. in solution.

The transphosphatidylation activity of some old preparations (2–5 years old) of phospholipase D from cabbage, stored at either−70° C. or −20° C., was found to be negligible or absent in the above biphasic water/ether system, while the hydrolase activity was largely maintained. However, all of these preparations were able to convert PC to PG in the water/silica gel system. Similar results were obtained with phospholipase D preparations that were stored in aqueous solutions at 4° C. These were totally inactive in the ether/water biphasic system but retained their full activity with silica gel, giving PC to PG conversions of more than 80%.

Because the transferase activity of the enzyme in the conventional ether/water biphasic system decreases with time, the enzyme is typically added to the reaction stepwise. However, in the water/silica gel system, the enzyme appears to be stable throughout the reaction, and may be added either stepwise or all at once with no effect on PG formation.

F. Effect of Direct Adsorption of Lipid onto Adsorbent

The formation of the liposomal suspension can be a time consuming process for a large-scale production. Therefore, the possibility of eliminating this step, by directly adsorbing the lipid from a chloroformic solution onto the silica powder, was examined. For this purpose, two 10 mg samples of PC were dissolved in 4 ml of $CHCl_3$ in round-bottomed flasks, and two amounts of silica gel 60H (Merck), 0.1 and 1.0 grams, respectively, were added. The chloroform was evaporated under reduced pressure. Acetate buffer, glycerol, $CaCl_2$ and enzyme were added to the dry powder, and the reaction was carried out essentially as described above. The procedure was repeated using magnesium silicate.

TLC chromatograms of samples taken after the reactions were terminated showed no production of PG in any case, indicating that this method of reaction is not viable, and suggesting that the reacting phospholipid must be dispersed in the buffer for the transphosphatidylation to take place.

G. Other Factors: Activation/Deactivation of Adsorbents: Liposome Size; Antioxidant These factors were found to have little or no effect on conversion in the above-described reaction. To test the effect of adsorbent activation/deactivation, the two types of adsorbents giving the best results in the reaction, i.e. silicic acid 60H (Merck) and magnesium silicate (Florisil®) (Bio-Rad), were submitted to heat activation (dehydration) and deactivation (hydration). The activation was performed by heating the adsorbents at 100° C. overnight and the deactivation by adding 0.2 ml of water homogeneously to 200 mg of the adsorbent powder. Conversions obtained with these treated adsorbents were compared with non-treated adsorbents (Example 3). TLC chromatograms showed similar conversions in all the systems tested, in the range of 50–60% PG production. It can therefore be concluded that dehydration or hydration of the adsorbent does not affect conversion, so there is no need for pretreatment of the adsorbent before the reaction.

Based on the assumption that conversion may be limited by the exposure of substrate to enzyme, the influence of the liposome size on the efficiency of the transphosphatidylation reaction was examined, using MLV (approx. 1.5 μm diameter) and SUV (20–40 mm diameter). The liposomal dispersions were formed and the reactions carried out as described in Example 4. About 40% PG production was observed in both systems, indicating that substrate availability is not limited by vesicle size.

The peroxidation of phospholipids having polyunsaturated acyl chains can be inhibited by the use of antioxidants. It was found that presence of the antioxidant butylated hydroxytoluene (BHT) did not affect the activity of silica-gel activated phospholipase D in the transesterification reaction. The antioxidant afforded excellent protection against lipid peroxidation during the reaction, allowing the production of high quality PG.

III. Further Scaleup

Reaction at a 5 gram scale (using egg PC prepared from fresh eggs) gave similar results to those at 500 mg scale. The scale was then increased to 20 grams, using commercial phospholipid from the Asahi Co. (Japan). Using the preferred conditions described in Section II above, but reducing the amount of silica gel to a silica gel/lecithin ratio of 4.0, a conversion of approximately 70% PC to PG was obtained after 4 hours of reaction. Most of the conversion occurred during the first hour. The level of PA was very low (<5%).

The reaction was also tested under industrial scale conditions using pilot plant reactors. A 100 gram scale process was carried out at the minipilot plant unit of the Casali Institute of Applied Chemistry, School of Applied Sciences, The Hebrew University, Jerusalem, as described in Example 5. The PG conversion was 40% at room temperature and 50% at 35° C. About 7% of PA was produced at room temperature, while at 35° C. a higher level of PA (15%) was observed.

IV. Variation of Lipid Substrate

Saturated phospholipids may be more suitable than unsaturated phospholipids for certain drug delivery systems, due to their higher resistance to lipid peroxidation. Partially hydrogenated (PH) egg PC is a potential candidate to replace egg PC. Therefore, the transphosphatidylation of PC to PG was tested with a saturated lipid, dipalmitoyl PC (DPPC; Avanti Polar Lipids, Birmingham, Ala.) and with partially hydrogenated (PH)PC (iodine value 30; Asahi Chemical, Japan). Reactions were carried out as described in Example 6. TLC of the DPPC reaction showed 50% conversion to DPPG and no trace of PA. A yield of 77% PH-egg PG was obtained from PH-PC, with only traces of PA (<5%) detected.

The results of these reactions and of additional substrates and hydroxyl-containing reagents are summarized in Table 9. The reaction gives good conversion for a variety of reagents and substrates, including tissue extracts. Phosphatidyl serine enrichment of a brain phospholipid extract (sixth row of Table 9) is described in more detail in Example 7.

TABLE 9

| Lipid Substrate | Reagent | Product | Typical Conversion |
|---|---|---|---|
| Egg lecithin (PC) | Glycerol | PG | 50–70% |
| Egg lecithin | Serine | PS | 70–90% |
| Egg lecithin | Water | PA | 70–100% |
| Egg lecithin | Myo-inositol | PI | 60–80% |
| Phosphatidyl ethanolamine | Glycerol | PG | 15–40% |
| Brain phospholipid extract | Serine | PS enrichment | 80% |
| Dioleyl PC | Glycerol | Dioleyl PG | 50–70% |
| Dipalmitoyl PC | Glycerol | Dipalmitoyl PG | 50% |
| Partially hydrogenated egg PC | Glycerol | PH-PG | 75–80% |

V. Reaction of Other Phospholipases

The biphasic water/silica gel method was employed for reaction of other phospholipases (C and A2) in selective hydrolysis of egg PC. Reactions were done on a 10 g scale, using Merck silica gel, 70–230 mesh. Other conditions and conversions (after 4 hrs at room temperature) are given in Table 10. Reaction with phospholipase C, under similar conditions, was also used to prepare ceramide from sphingomyelin (data not shown).

TABLE 10

| Phospho-lipase | Source of enzyme | Medium | Product | Typical Conversion |
|---|---|---|---|---|
| C | *Clostridium welchii* (Sigma) | Tris buffer (40 mM, pH 7.6) 20 mM $Ca^{+2}$ | Diacyl glycerol | 100% |
| C | *Bacillus cereus* (Makor) | Tris buffer (40 mM, pH 7.6) 20 mM $Ca^{+2}$ | Diacyl glycerol | 70–90% |
| A2 | Snake venom Naja-Naja (Sigma) | Acetate buffer (40 mM, pH 5.6) 100 mM $Ca^{+2}$ | Lyso-lecithin | 100% |
| A2 | *Crotalus adamaneus* (Sigma) | Acetate buffer (40 mM, pH 5.6) 100 mM $Ca^{+2}$ | Lyso-lecithin | 100% |

EXAMPLES

The following examples illustrate but are not intended in any way to limit the invention.

EXAMPLE 1

Isolation of Phospholipase D from Cabbage

A. Standard Preparation

Phospholipase D was prepared from Savoy cabbage according to the procedure of Yang. A crude extract was first prepared by homogenizing 4250 kg of light-green leaves of fresh Savoy cabbage with distilled water in a Waring blender. The fibrous material was removed by filtering through a gauze. The final volume of the cabbage juice (3750 liters) was then centrifuged at 500 g for 5 minutes at 4° C. The extract was heated to 55° C., maintained at this temperature for 5 minutes, and then rapidly cooled. The bulky precipitate was removed by centrifugation under the same conditions and discarded.

Two volumes of acetone were added to the supernatant at −15° C., and the mixture was shaken immediately and stored overnight at 4° C. The acetone was evaporated and the aqueous suspension was centrifuged. The supernatant was discarded and the precipitate lyophilized overnight under 150 millitorr vacuum. The enzyme, obtained as a light green powder (5.2 g), was stored frozen at −70° C. until needed.

It was later found that the yield of enzyme powder could be improved by reducing the volume of water used for the homogenization of the cabbage leaves. The modified procedure yielded 2.6 grams of lyophilized protein per kilogram of cabbage.

B. Simplified Preparation

It was found that by replacing the slow speed centrifugation step (500 g×15 min. at 4° C.) of the above method with high speed centrifugation (15000 g×15 min. at 4° C.), the supernatant could be used as the enzyme preparation without further purification. The high speed centrifugation yields reproducible enzyme preparations free of particulate and fibrous matter. No cabbage residual lipids were detected in the extract, using the method of Bligh and Dyer. The centrifugation step could be further optimized to fit industrial needs by using continuous flow centrifugation. Using this crude fresh enzyme, similar conversions of PC to PG were obtained at similar equivalents of protein weight per cabbage weight using the experimental conditions described above.

EXAMPLE 2

Determination of Conversion

Lipids are extracted from the incubation mixture by vortexing with a 1:1:1 mixture of chloroform:methanol:water and allowing the phases to separate. The upper aqueous-methanolic phase contains all the water soluble reagents, while the lower chloroformic phase contains the lipids (e.g. PC, PG and phosphatidic acid (PA)). Aliquots of the lower phase are loaded on Analtech silicic acid thin layer on a glass plate for TLC. The phospholipids are separated (FIG. 1) using a solvent system of chloroform:acetone:mezhanol:acetic acid:water (6:8:2:2:1 v/v). The individual spots are scraped into phosphorous free test tubes, and the phosphorous content is determined using the perchloric acid based Bartlet procedure (see e.g. Barenholz et al., 1993).

An alternative assay for assessing conversion, based on the use of a radioactive water soluble reagent, was developed during the course of this work. For example, tritiated glycerol or serine is used; i.e. $^3$H-glycerol (or serine)+ PC→$^3$H-PG (or $^3$H-PS)+choline (+PA). The glycerol or serine partitions into the upper methanolic/aqueous phase in the biphasic solvent system of chloroform:methanol:water (8:4:3 or 1:1:1) during workup; all lipids partition into the chloroform lower phase. $^3$H-PG or $^3$H-PS is determined by scintillation counting of the chloroform phase.

This assay was tested under various conditions and proved to be simpler and much faster than thin layer chromatography. However, it does not determine the level of PA (undesired product).

A spectrophotometric method suitable for the determination of amine phospholipids (i.e. PS or PE) utilizes the reaction of the amine phospholipid with trinitro benzene sulfonate (TNBS) to form the yellow trinitrophenyl derivative (i.e. TNP-PS). This product is determined spectrophotometrically in the chloroform enriched lower phase (Barenholz et al., 1993) or by TLC (Amselem et al., 1993).

EXAMPLE 3

Conversion of PC to PG using Activated or Deactivated Adsorbent

Egg PC (10 mg) was dispersed in 0.5 ml of 50 mM acetate buffer (pH 5.6) containing 50 mM $CaCl_2$ and 50% (vol) glycerol. Cabbage phospholipase D (Boehringer) was added (0.5 mg), and the reaction was started by adding 200 mg of silicic acid or Mg-silicate as normal powder, activated or deactivated. The reaction mixtures were shaken at room temperature for 30 minutes. The reactions were terminated by adding 0.5 ml of distilled water and 2 ml of a $CHCl_3$:methanol mixture (1:1). The lipids were extracted from the lower phase after centrifugation.

EXAMPLE 4

Reaction of PC in SUV and MLV

The reactions were carried out on a 5 gram (PC) scale. The lipid was dissolved in 100 ml $CHCl_3$. Glass beads (100 grams) of 5 mm diameter were added to increase the surface area of the dried lipid film and to ensure a better dispersion of the lipid in the aqueous solution. The organic solvent was removed by a flash evaporator. Then 50 ml of the acetate buffer containing 50% glycerol was added, and the MLV were formed by shaking the mixture in a Lap-line multi-wrist shaker until an homogeneous liposomal dispersion was obtained. The SUV were prepared from these MLV by sonicating the MLV using a probe sonicator (350 heat systems, Ultrasonics Inc.) for 5 minutes. At the same time, 600 grams of cabbage were homogenized in a Waring blender with 250 ml acetate buffer, filtered through a gauze and centrifuged for 20 minutes at 4° C. at 15,000 rpm. Fifty mL of this fresh crude supernatant were mixed with 25 grams glycerol and added to the MLV and to the SUV. The reactions were initiated by adding 25 grams silica gel 60H, the mixture was shaken overnight at room temperature in the multi-wrist shaker.

EXAMPLE 5

Large Scale Conversion of PC to PG

MLV were prepared by the thin lipid film procedure. Egg phosphatidylcholine (100 grams) from Asahi Co. (Japan) was dissolved in 500 ml $CHCl_3$ in a 1 liter round bottomed flask. The antioxidant BHT (butylated hydroxytoluene) was added at a molar ratio of 1/1000. Glass beads (400 gram) were added, and the organic solvent was evaporated until dryness. Acetate buffer (pH 5.6, 1 liter) containing 50% glycerol and 0.1 M $CaCl_2$ was added, and MLV were formed by vigorous shaking of the mixture for 1 hour with the aid of the multi-wrist shaker. The final volume of the MLV prepared was divided into two 0.5 liter portions. To each portion was added 250 ml additional acetate buffer, and the mixtures were introduced in two minireactors of 1.5 liter capacity. Fresh crude cabbage phospholipase D juice (250 ml), diluted 1:1 with glycerol to give a final concentration of 50% glycerol, was added to each minireactor. The temperatures in the two reactors were room temperature (20° C.) and 35±5° C., respectively. Silica gel 60H (Merck) (250 g) was added to each reactor. Mixing of reagents in the reactors with mechanical shaking. The reactions were carried out under a nitrogen atmosphere. After 20 hours of reaction, the shaking was stopped, and 1 ml samples were taken from the bottom of each reactor. Each sample was extracted by adding 1 ml DDW and 2 ml of 1:1 $CHCl_3$:methanol. The phases were separated by centrifugation and aliquots of the lower phases were analyzed by TLC, eluting with $CHCl_3$:acetone:acetic acid:$H_2O$ (6:8:2:2:1). The spots were scraped and extracted and the phospholipid content determined by the Bartlett procedure.

EXAMPLE 6

Reaction of Saturated and Partially Hydrogenated Lipids

MLV were prepared, using 10 mg DPPC in 10 ml acetate buffer (pH 5.6) containing 50% glycerol and 100 mM $CaCl_2$ at 55° C. (10° C. above $T_m$). Ten mL phospholipase D solution, prepared in house, were mixed with 5 gams glycerol and added to the DPPC-MLV. The reaction was started by adding 2.5 grams silica gel 60H, and the mixture was shaken for one hour at room temperature.

PH-egg PC lipid (5 grams) was dried from chloroform solution on 100 gram glass beads (5 mm diameter). Acetate buffer (450 ml, containing glycerol and $CaCl_2$ as described above) was added, and MLV were formed by shaking the mixture vigorously for 1 hour with a Lab-line multi-wrist shaker. A solution of 20 mg of cabbage phospholipase D (Boehringer) dissolved in 5 ml acetate buffer was then added. The reaction was started by adding 125 grams silica gel 60H (Merck), the mixture was shaken overnight at room temperature.

EXAMPLE 7

Phosphatidyl Serine Enrichment of Brain Phospholipid Extract

Bovine brain phospholipid extract containing 15 mole % PS, 43 mole % PC, and 34 mole % PE was used. MLV were prepared from the extract as described in example 5. L-Serine (powder) was added to the liposomal dispersion at a level close to saturation. Fresh crude cabbage juice (Example 1 simplified procedure) was used as the enzyme source. The reaction was carried out as described in Example 5. Analysis by the TNBS method and by the TLC method, described above, showed that the level of PS was increased from 15 mole % in the starting material to 51 mole % in the final product.

A similar reaction using D,L-serine gave 49 mole % phosphatidyl serine in the final product.

While the invention has been described with reference to specific methods and embodiments, it will be appreciated that various modifications may be made without departing from the invention.

It is claimed:

1. A method of conducting an enzyme-catalyzed transesterification or hydrolysis of a phospholipid, comprising
   dissolving said enzyme in an aqueous medium containing (i) a liposomal suspension of said phospholipids, (ii) a hydroxyl-containing reagent selected from water, an alcohol or an alcohol derivative, and (iii), when required by the enzyme, a divalent metal cation,
   adding silica gel to said medium, and agitating the resulting mixture.

2. The method of claim 1, wherein the enzyme is selected from the group consisting of phospholipase A1, phospholipase A2, phospholipase C, phospholipase D, and a sphingomyelin phosphodiesterase.

3. The method of claim 2, wherein the enzyme is selected from the group consisting of phospholipase A2, phospholipase C, and phospholipase D.

4. The method of claim 3, wherein the enzyme is phospholipase D.

5. The method of claim 4, wherein the divalent metal cation is calcium ion in concentration of about 5–100 mM.

6. The method of claim 1, wherein the hydroxyl-containing reagent is an alcohol or alcohol derivative.

7. The method of claim 6, wherein the hydroxyl-containing reagent is selected from the group consisting of glycerol, serine, and inositol.

8. The method of claim 6, wherein the hydroxyl-containing reagent is a hydroxy-terminated polyethylene glycol having a molecular weight between about 300 and 40,000.

9. The method of claim 1, wherein the silica gel is added in an amount which is at least four times the amount of the phospholipid by weight.

10. The method of claim 9, wherein the silica gel is added in an amount which is at least ten times the amount of the phospholipid by weight.

11. The method of claim 1, wherein the silica gel has a mean particle size no greater than 25 $\mu$m.

12. The method of claim 11, wherein the silica gel has a mean particle size no greater than 15 $\mu$m.

13. The method of claim 1, wherein the phospholipase is present in said medium at a concentration of at least 3 mg/ml.

14. The method of claim 13, wherein the phospholipase is present in said medium at a concentration of at least 7 mg/ml.

15. A method of conducting an enzyme-catalyzed transesterification or hydrolysis of a phospholipid, comprising
    dissolving said enzyme in an aqueous medium containing (i) a liposomal suspension of said phospholipid, and (ii) a hydroxyl-containing reagent selected from water, an alcohol or an alcohol derivative,
    adding silica gel to said medium, and agitating the resulting mixture.

16. The method of claim 15, wherein said aqueous medium further contains (iii) a divalent metal cation.

* * * * *